(12) United States Patent
Bushy

(10) Patent No.: US 12,090,287 B2
(45) Date of Patent: Sep. 17, 2024

(54) CATHETER SHIELD

(71) Applicant: Ita Bushy, Sherman Oaks, CA (US)

(72) Inventor: Ita Bushy, Sherman Oaks, CA (US)

(*) Notice: Subject to any disclaimer, the term of this patent is extended or adjusted under 35 U.S.C. 154(b) by 0 days.

(21) Appl. No.: 17/224,383

(22) Filed: Apr. 7, 2021

(65) Prior Publication Data

US 2021/0308426 A1     Oct. 7, 2021

Related U.S. Application Data

(60) Provisional application No. 63/006,280, filed on Apr. 7, 2020.

(51) Int. Cl.
    *A61M 25/02*      (2006.01)

(52) U.S. Cl.
    CPC ..... *A61M 25/02* (2013.01); *A61M 2025/0246* (2013.01); *A61M 2025/0266* (2013.01); *A61M 2205/0205* (2013.01)

(58) Field of Classification Search
CPC .......... A61M 25/02; A61M 2025/0246; A61M 2025/0266; A61M 2205/0205; A61F 5/445; A61F 2013/00412; A61F 5/443; A61F 13/42; A61F 2013/00889; A61F 13/023; A61F 5/448; A61F 2013/00604
See application file for complete search history.

(56) References Cited

U.S. PATENT DOCUMENTS

| | | | |
|---|---|---|---|
| 3,598,123 A * | 8/1971 | Zaffaroni | A61K 9/7061 424/435 |
| 5,605,546 A * | 2/1997 | Wolzinger | A61M 25/02 604/174 |
| 9,204,990 B1 | 12/2015 | Berven | |
| 9,579,487 B2 | 2/2017 | Ambrose | |
| 10,137,292 B2 | 11/2018 | Dabel | |
| 2004/0044299 A1* | 3/2004 | Utsugi | A61F 13/0246 602/58 |
| 2006/0263597 A1* | 11/2006 | Birkholz | G01N 31/222 428/354 |
| 2007/0055205 A1* | 3/2007 | Wright | A61F 15/004 424/447 |
| 2007/0282271 A1 | 12/2007 | Kaplan | |
| 2008/0167626 A1 | 7/2008 | Beery | |

(Continued)

FOREIGN PATENT DOCUMENTS

| | | |
|---|---|---|
| EP | 0671182 A1 | 11/1995 |
| JP | 4295677 B2 | 7/2009 |

*Primary Examiner* — Tiffany Legette

(74) *Attorney, Agent, or Firm* — Fitzpatrick PC Attorneys at Law; William Fitzpatrick

(57) ABSTRACT

A catheter shield is described herein. The catheter shield has a sleeve configured to receive and house a proximal end of a catheter projecting from a patient, a retention structure configured as an outer protective barrier, a first adhesive layer disposed on a bottom portion of the retention structure, wherein the first adhesive layer provides adherence to the patients skin; a second adhesive layer provided on an outer edge of the sleeve and located within a diameter of the retention structure, wherein the second adhesive layer is configured as a middle protective barrier, a third adhesive layer located within a diameter of the second adhesive, wherein the third adhesive is layer is configured as an inner protective barrier, and wherein the third adhesive layer comprises a moisture indicator posited thereon.

11 Claims, 6 Drawing Sheets

(56) References Cited

U.S. PATENT DOCUMENTS

| | | | |
|---|---|---|---|
| 2008/0208145 A1 | 8/2008 | McCulloch | |
| 2009/0247965 A1 | 10/2009 | Williams | |
| 2013/0317445 A1* | 11/2013 | Steer | A61M 25/02 |
| | | | 604/180 |
| 2015/0196590 A1* | 7/2015 | Sampson | A61K 45/06 |
| | | | 424/661 |
| 2017/0246435 A1* | 8/2017 | Oveland | A61M 25/0108 |
| 2017/0340864 A1* | 11/2017 | Rios | A61M 25/02 |
| 2020/0046570 A1* | 2/2020 | Sheridan | A61F 13/0233 |
| 2021/0236777 A1* | 8/2021 | Chelak | A61M 39/12 |

\* cited by examiner

CATHETER SHIELD

CROSS-REFERENCE TO RELATED APPLICATION

This application claims the benefit of U.S. Provisional Application Ser. No. 63/006,280 entitled Catheter Shield filed on Apr. 7, 2020, the entire contents of which are incorporated herein by reference for all purposes.

FIELD OF THE INVENTION

The present invention relates generally to medical devices. More particularly, the present invention relates to a water, bacteria and virus-resistant catheter shield.

BACKGROUND OF THE INVENTION

A catheter is a thin tube or line that is inserted through the skin into the body cavity, duct or vessel to fluidly communicate with the vascular system (e.g., bladder, heart, stomach lining) of a patient. The catheter may be placed in various parts of the body such as arm, hand, neck, stomach or chest. There are a wide variety of catheters that are ancillary to various medical procedures, and these catheters have many uses.

Medical catheters are tubes that can be inserted into a body cavity, vessel or duct, usually to allow for the administration of fluids, medications or gases or to drain fluids or urine from the body. Examples of some types of catheter include intravenous catheters, urinary catheters and chest drainage tubes. Uses of catheters include Foley's catheters in which the catheter is inserted into the bladder where it is held in place by a balloon filled with sterile water. Urine drains through the catheter into a bag that can be emptied. It may be used in cases of urine retention, interrupted urine stream, straining on urination, obstructed urethra or for the monitoring of urine output in a critically ill patient as well as after surgery. In a procedure called percutaneous nephrostomy, catheters may be used to drain urine from the kidney. Catheters may be used to drain fluid and pus that is collecting in cavities. For example, they may be used to drain pus from an abdominal abscess.

Catheters are also used for intravenous fluid and drug administration. In these cases, a fine, thin tube is inserted into the vein to deliver fluid or medication to the patient. Infusion pumps are connected to catheters to deliver medications to patients, for example to deliver chemotherapy to cancer patients or insulin to diabetic patients. Central venous catheters are large tubes that are placed directly into large veins in the neck or into the atrium of the heart to deliver medication or fluids. In sick newborns, an umbilical line may be created for delivering medication and fluids. Cardiovascular procedures such as angioplasty, angiography, and balloon septostomy all use catheters. A catheter is inserted into a vein in the groin and threaded into the heart under the guidance of X-ray imaging.

Catheters used in cardiology procedures may be designed to measure blood pressure in an artery or vein at specific locations in the body. The Swan-Ganz catheter is a special type of catheter placed into the pulmonary artery for measuring pressure in the heart. These can also be used for the direct measurement of pressure within the brain. Catheters are also used in regional anesthesia such as spinal and epidural anesthesia. The catheter can deliver anesthetic medication into the epidural space, the subarachnoid space, or around a major nerve junction in order to numb or paralyze certain locations.

Catheters may also be used for treating diseases, obtaining body fluids, administering medications, collecting stem cells, monitoring pressure, dialysis, and other surgical procedures.

With all the-above recited uses, there are at least two significant concerns for patients using catheters: Keeping the area dry and keeping the area clean to lower the risk of infection. Catheters requires high maintenance to protect from various matter such as water, dirt, dust, sweat, humidity, bacteria, and virus. Thus, the patient is often severely limited to perform their normal daily activities, such as taking showers or baths, as moisture may support the growth of harmful or infectious microorganisms. For example, bacteria and fungus may form in and around the exit site of the catheter. Further, patients using catheters are at increased risk of blood stream infections. \

Some current catheter protectors or shields only protect the entry site into the skin and are not water resistant Other shields are water-resistant and used to prevent water running on the catheter. However, these shields do not prevent contaminants from making contact with the catheter or entry site into the skin.

Further, some shields, for example, gauze bandage and tape, easily fall off and absorb moisture, dead skin cells, and bacteria. These shields promote infection instead of preventing it.

In fact, 3% to 8% of inserted catheters are the first cause of nosocomial bloodstream infection in intensive care units (ICUs), with 80,000 cases annually at a cost of $300 million to $2.3 billon. Additional financial costs may be as high as $30,000 per survivor, including one extra week in the ICU and two to three additional weeks in the hospital. Attributable mortality rates range from 0% to 35%, depending on the degree of control for severity of illness.

The extraluminal and intraluminal routes migration of skin organisms from the insertion site into the cutaneous catheter tract with colonization of the catheter tip is the most common route of infection for short-term central venous catheters (CVCs). For long-term catheters (i.e., catheters staying in place more than 15 days), the main cause of colonization is manipulation of the venous line with migration of organisms along the internal lumen of the catheter. The adherence properties of microorganisms to host proteins, such as fibronectin, commonly present on catheter tips make this colonization easier. Coagulase-negative staphylococci are the most common microorganisms associated with catheter-related bloodstream infections. Other microorganisms commonly involved include *Staphylococcus aureus*, *Candida* species, Enterococci and Gram-negative bacilli.

An exemplary protector or shield is shown in FIG. 1. The shield device 100 covers the catheter positioned on a user's skin. The catheter covering device 100 comprises a water-resistant sleeve 102 having a first end and a second end. The first end is open end whereas the second end is closed end. The first end has a rim 104 forming an opening into the sleeve 102. An adhesive film 106 with a release line is attached to the rim 104 of the sleeve 102. Further, the adhesive film 106 has a tab 108 that extends outwards from the perimeter of the adhesive film 106. The catheter cover device 100 is adhered to the user's skin using adhesive film 106 by removing the release line.

Another type of shield is disclosed in U.S. Ser. No. 10/137,292 to Pascal that discloses a method of covering a catheter attached to a body. The catheter covering device comprises of at least a sleeve and an adhesive film. The catheter covering device includes a water indicator attached to the adhesive film and a desiccant paper attached to the water indicator. The adhesive film may include a larger diameter than the water indicator and the desiccant paper. If moisture enters the catheter covering device, the desiccant paper may absorb the moisture and activate the water indicator, indicating to the user that the catheter covering device has been contaminated and white to red color change is visible through the device.

Yet another type of shield disclosed in prior art patent, US20130317445 assigned to Graham discloses an apparatus for shielding a catheter from contact with water whilst showering. This apparatus is worn by a patient, to resist water contact with exit aperture without obstructing access to an area of the patient's skin beneath second part of first shield component. The adhesive may extend along more than one peripheral side of second shield component. However, the existing prior still lacks to provide an effective and comfortable shield for shielding the catheter.

The current devises have multiple drawbacks, including but not limited to skin irritation and in some instances causing of abrasions, ineffective moisture indicators, and improper size.

In light of all the above-mentioned drawbacks, there is a need for a water-resistant catheter shield that protects the catheter from moisture and provides increased hygiene for an improved quality of life of the user.

SUMMARY OF THE INVENTION

To achieve the foregoing and other aspects and in accordance with the purpose of the invention, the subject invention provides a water-resistant and bacteria, fungus and virus mitigating catheter shield for covering the indwelling catheter from contact with water.

In one embodiment, the catheter shield comprises a fluid-impermeable sleeve having a first end and a second end. In one embodiment, the first end comprises an opening and second end comprises an adhesive patch. In one embodiment, a catheter retention structure is disposed at the opening of the sleeve. In one embodiment, the sleeve is configured to receive and house a proximal end of the catheter projecting from a patient's skin via the opening at the first end.

The catheter retention structure is a rib for impeding the motion of the proximal end of the catheter. In one embodiment, the catheter retention structure is rectangular in shape. A moisture indicator of rectangular shape is disposed around the opening of the sleeve. The moisture indicator includes a rectangular opening that leads into the sleeve.

In embodiments, a catheter shield comprising a sleeve configured to receive and house a proximal end of a catheter projecting from a patient, a retention structure configured as an outer protective barrier, a first adhesive layer disposed on a bottom portion of the retention structure, wherein the first adhesive layer provides adherence to the patients skin, a second adhesive layer provided on an outer edge of the sleeve and located within a diameter of the retention structure, wherein the second adhesive layer is configured as a middle protective barrier, a third adhesive layer located within a diameter of the second adhesive, wherein the third adhesive is layer is configured as an inner protective barrier, wherein the third adhesive layer comprises a moisture indicator posited thereon.

The catheter shield further comprises a first adhesive film, a second adhesive film, and a third adhesive film. In one embodiment, the first adhesive film is disposed around a perimeter of the moisture indicator and the second adhesive film is disposed around the first adhesive film. In one embodiment, the third adhesive film extends from a brim of the second adhesive film. In one embodiment, the catheter shield further comprises one or more release papers disposed in a rectangular array over the first, second and third adhesive films. At least two tabs extends from each release paper. Each of the layers of the shield may be manufactured from various plastics such as polyethylene, may be EtO, e-beam, x-ray or gamma sterilized, and be hypoallergenic. Other layers may comprise lubricating mediums, such as beeswax, glycerin, anhydrous lanolin, lanolin alcohol, mineral oil, paraffin, petrolatum, petroleum jelly, shark liver oil, thyme oil, or the like.

In embodiments, the first adhesive may comprise a pressure sensitive acrylic (PSA), as for example, from Avery Dennison® or 3M®. Acrylic pressure-sensitive adhesives are made with several types of acrylic monomers that are polymerized to high molecular weight polymers. Generally, acrylic adhesives are formulated with polymers of relatively low molecular weight and Tg so that they are inherently soft at ambient temperatures. Silicone based PSA may be used as well.

In embodiments, the first adhesive may comprise silicone PSA having a multiple (e.g., five) layer silicone foam border dressing, a soft coating, a transparent PU film, the latter being a two-part transparent solvent based polyurethane resin coating. It is specially provided as a durable, UV resistant protective coating system. Further, the adhesive may be a clear PU film with a high tack silicone adhesive, or a white PE Non-woven fabric coated with a repositionable acrylic adhesive, or a clear PU film with a standard acrylic adhesive and a paper support film.

Each of the layers and adhesives are compatible with Gamma and ETO sterilization, and are sterilized using either of these (or additional) sterilization processes prior to shipping.

In embodiments, materials may be injection molded from a waterproof, light weight, pliable yet sturdy, durable, easily sanitized material such as medical grade silicone rubber. However, the protector sheath can be composed of any other material that possesses the desired properties and/or qualities. The material can be transparent, translucent, semi-translucent, opaque, or colored, and be medical grade absorbents and medical grade adhesives. Plastics that may be used in the construction of the catheter shield include but are not limited to Polypropylene PP including OPP and BOPP, Polycarbonate (lexan, acrylic), Polyethylene HDPE and LDPE, Polyvinyl Chloride (PVC) and Polyurethane Film.

The layers may further be treated with an anti-infective dressings to obviate the openings bioburden and reduce the risk of infection over percutaneous line sites.

The device has multiple advantages over prior art designs. For example, the shield provides a water-resistant catheter shield for covering the indwelling catheter from contact with water and provides multiple redundancies and moisture notification elements.

Further, the shield provides a water-resistant catheter shield to protect indwelling medical devices, during shower, bathing, or swimming while also protecting skin to skin contact.

Further, the shield protects and prevent the growth of harmful or infectious bacteria, microbes and fungus, and moisture in and around the user's or patient's skin because of the hyprochlorous acid or chlorine dioxide impregnated layer and/or other anti-infective dressings or impregnations.

Other features, advantages, and aspects of the present invention will become more apparent and be more readily understood from the following detailed description, which should be read in conjunction with the accompanying drawings.

BRIEF DESCRIPTION OF THE DRAWINGS

The present invention is illustrated by way of example, and not by way of limitation, in the figures of the accompanying drawings and in which like reference numerals refer to similar elements and in which.

DETAILED DESCRIPTION OF THE PREFERRED EMBODIMENTS

Figure 1:
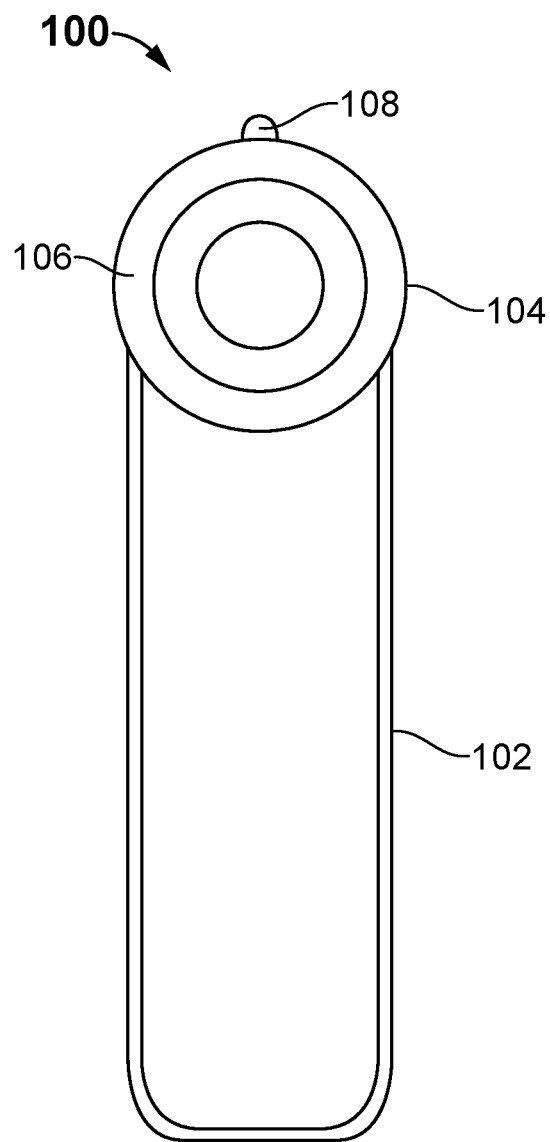
FIG. 1 is a prior art catheter shield.

The present invention is best understood by reference to the detailed description and examples set forth herein.

Embodiments of the invention are discussed below with reference to the examples. However, those skilled in the art will readily appreciate that the detailed description given herein with respect to these examples is for explanatory purposes as the invention extends beyond these limited embodiments. For example, it should be appreciated that those skilled in the art will, in light of the teachings of the present invention, recognize a multiplicity of alternate and suitable approaches, depending upon the needs of the particular application, to implement the functionality of any given detail described herein, beyond the particular implementation choices in the following embodiments described and shown. That is, there are numerous modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

It is to be further understood that the present invention is not limited to the particular methodology, compounds, materials, manufacturing techniques, uses, and applications, described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" is a reference to one or more steps or means and may include sub-steps and subservient means. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

Unless defined otherwise, all technical and scientific terms used herein have the same meanings as commonly understood by one of ordinary skill in the art to which this invention belongs. Preferred methods, techniques, devices, and materials are described, although any methods, techniques, devices, or materials similar or equivalent to those described herein may be used in the practice or testing of the present invention. As used herein, the term "anti-infective" comprises anti-bacteria, antifungal, and anti-virus agents. Anything that is capable of inhibiting the spread of an infectious organism or by killing the infectious organism outright. This term encompasses antibiotics, antifungals, anthelmintics, antimalarials, antiprotozoals, antituberculosis agents, and antivirals.

Figure 2:
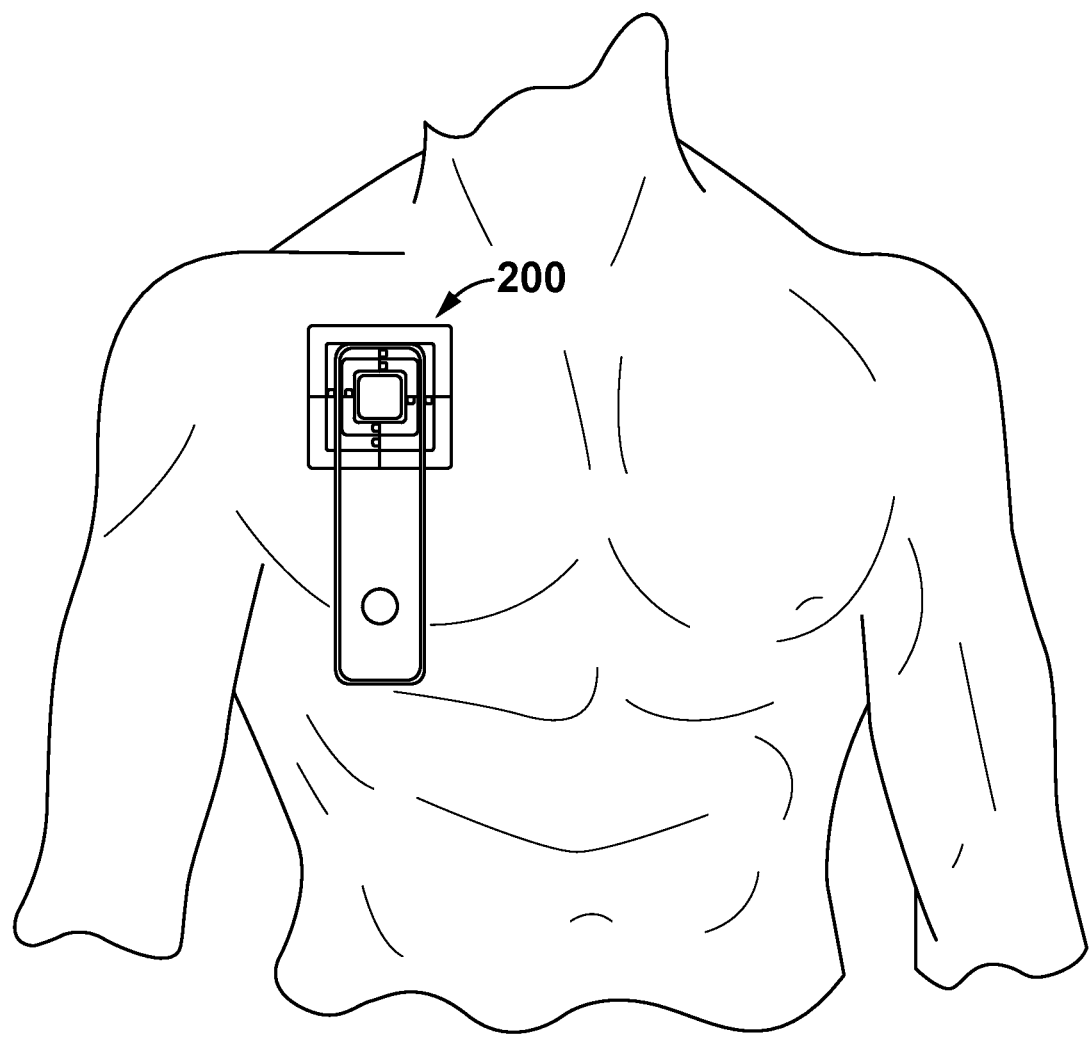
FIG. 2 illustrates a water, bacterial, virus and fungal-resistant catheter shield installed on an indwelling catheter, according to an embodiment of the present invention.

Referring now to FIG. 2, the catheter shield 200 is shown attached to a user. In this embodiment, the catheter shield is used for with a central venous catheters are large tubes that are placed directly into large veins in the neck or into the atrium of the heart to deliver medication or fluids. The catheter shield 200 is applied or attached to the user via a plurality of layers on the shield 200 having multiple different adhesives as described in more detail with relation to FIG. 3.

Figure 3:
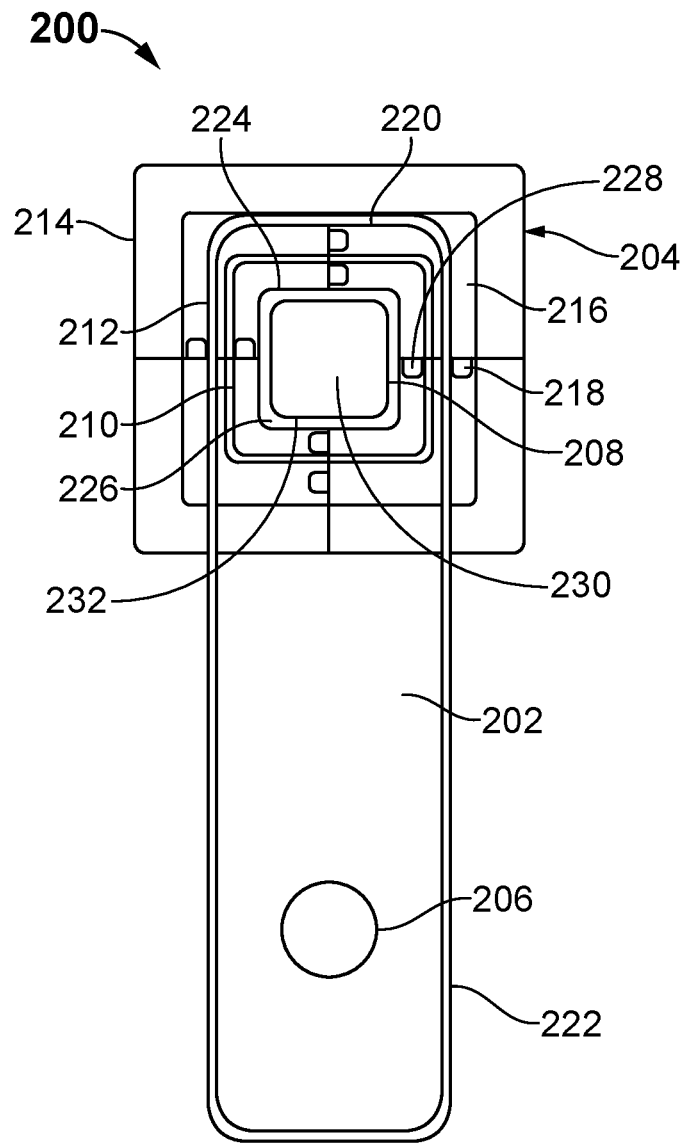
FIG. 3 illustrates a front view of the catheter shield, according to an embodiment of the present invention.

Referring now to FIG. 3, the catheter shield 200 comprises a sleeve 202 which is formed together with retention structure 204, each of which comprise their own first and second adhesive layers 214, and 212, respectively. The sleeve 202 is configured to receive and house a proximal end of the catheter projecting from a patient's skin via the opening 230 toward the first end 220. The catheter retention structure 204 is a rib for impeding the motion of the catheter. The catheter retention structure is a rectangular shape disposed around the opening 206 of the sleeve 202 but may include opening of any desired shape.

The sleeve 202 may be made of fluid-impermeable material that is flexible and configured to cover or house the catheter elements connected to the patient's body. The sleeve 202 may made of, including, but not limited to plastics, polymer, latex, or rubber. Exemplary materials include Polypropylene comprising OPP and BOPP, Polycarbonate (lexan, acrylic), Polyethylene HDPE and LDPE, Polyvinyl Chloride (PVC) and Polyurethane Film.

The retention structure 204 is located at the bottom of the catheter shield 200 such that it acts as the first and outermost layer that adheres to the patients skin. The retention structure 204 comprises a first adhesive 214 located on the back side of the retention structure 204 so that the user may peel off a layer of release paper 216 located on the back of the retention structure 204 from the catheter shield 200 and use this first adhesive 214 to apply it to their skin. The user may use a first set of tabs 218 to peel off the release paper 216. However, prior to doing so, the user may apply a skin soothing lotion to avoid discomfort when removing the adhesive. In this way, to ensure adherence even over a lotioned portion of the skin, the adhesive may comprise a pressure sensitive acrylic (PSA), as for example, from Avery Dennison® Acrylic pressure-sensitive adhesives are made with several types of acrylic monomers that are polymerized to high molecular weight polymers. Generally, acrylic adhesives are formulated with polymers of relatively low molecular weight and Tg so that they are inherently soft at ambient temperatures. In other embodiments, the first adhesive may comprise silicone PSA having a multiple (e.g., five) layer silicone foam border dressing, a soft coating, a transparent PU film, the latter being a two-part transparent solvent based polyurethane resin coating. It is specially provided as a durable, UV resistant protective coating system. Further, the adhesive may be a clear PU film with a high tack silicone adhesive, or a white PE non-woven fabric coated with a repositionable acrylic adhesive, or a clear PU film with a standard acrylic adhesive and a paper support film.

Referring still to FIG. 3, sleeve 202 is formed together or connected to the retention structure 204, the attached points being shown at the top end 220 down toward the right and left side of the sleeve. In this way, the sleeve 202 is anchored to the retention structure 204 at the top end 220 and adheres to the users skin at a bottom end 222. The sleeve 202, at least on the portion of the sleeve that is within the retention structure 204, comprises a second adhesive layer 212 on its outer edge. The second adhesive layer 212 is located on the back side of the sleeve as a thin strip surrounding the sleeve. It is noted that the second adhesive only be located on portions within the diameter of the retention stricture 204, or may be located around the entire sleeve 202 in some embodiments. A second set of tabs 228 are located in the inner portion 224 of the shield 200 so that the user may peel off another layer of release paper (not shown) located on the back outer rim of the sleeve 202. This second adhesive 212 may, via application of pressure, adhere to the user's skin inside of the first adhesive 214 on the retention stricture forming a second layer of water, bacteria, fungal and virus protection. The second adhesive 212, like the first adhesive 214, may comprise a pressure sensitive acrylic (PSA), as for example, from Avery Dennison®. In other embodiments, the second adhesive 212 may comprise silicone PSA having a multiple (e.g., five) layer silicone foam border dressing, a soft coating, a transparent PU film, the latter being a two-part transparent solvent based polyurethane resin coating. It is specially provided as a durable, UV resistant protective coating system. Further, the second adhesive 212 may be a clear PU film with a high tack silicone adhesive, or a white PE Non-woven fabric coated with a repositionable acrylic adhesive, or a clear PU film with a standard acrylic adhesive and a paper support film.

Referring still to FIG. 3, within the diameter (or outer edges) of the retention structure 204, and further within the diameter of the sleeve 202 portion within the retention structure 204, a third adhesive layer 210 is provided. The third adhesive layer 210 is located on the back side of the sleeve 202 as a rectangular thin strip surrounding the opening 230. A third tab 226 is located in the inner portion 208 of the shield 200 so that the user may peel off another layer of release paper (not shown) located on the inner-back of the sleeve 202. This third adhesive 210 may, via application of pressure, adhere to the user's skin inside of the first adhesive 214 and the second adhesive 212 forming a third layer of water, bacteria, fungal and virus protection. The third adhesive 210, like the first and second adhesive 214 and 212, may comprise a pressure sensitive acrylic (PSA), as for example, from Avery Dennison®. In other embodiments, the second adhesive 212 may comprise silicone PSA having a multiple (e.g., five) layer silicone foam border dressing, a soft coating, a transparent PU film, the latter being a two-part transparent solvent based polyurethane resin coating. It is specially provided as a durable, UV resistant protective coating system. Further, the third adhesive 210 may be a clear PU film with a high tack silicone adhesive, or a white PE Non-woven fabric coated with a repositionable acrylic adhesive, or a clear PU film with a standard acrylic adhesive and a paper support film.

The third adhesive layer 210 may also have a moisture indication layer 232. The moisture indication layer 232 may be formed together with the third adhesive layer or on the outer rim of the third adhesive layer 210. In embodiments, the moisture indicator 232 changes color, when moisture comes into contact with the moisture indicator 232. This indicates the user that moisture has entered at the percutaneous puncture site of an indwelling catheter and the user may exit the water and remove the shield 200 and replace with a new device. The materials for the indicator may comprise hydrocolloid adhesive, melinex polyester film, and/or ethylene oxide.

In this way, should all layers fail to keep water out, the user will be notified via a color change of the moisture indicator 232, but still have the third adhesive layer in place to protect the catheter insertion point or aperture 230. Furthermore, this layer may further comprise a biological indicator to allow the user to see if bacteria is near insertion point (e.g., bacteria or fungus or infectious agents has gotten past the first layers).

Each of the layers may be impregnated with a purification layer such as hypochlorous acid or chlorine dioxide or other salts, or may be microcapsuled with anti-infectives. In one embodiment, the layers be made of polyethylene that is EtO or gamma sterilization, hypoallergenic sterilization, hydrocolloid adhesive and may be hydrophobic or hydrophilic.

Figure 4:
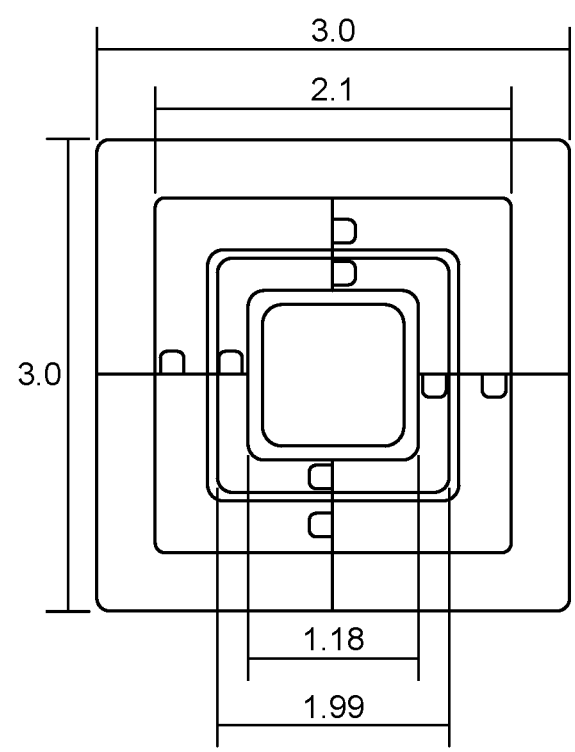
FIG. 4 illustrates a front view of a catheter retention structure, according to an embodiment of the present invention.

Referring now to FIG. 4, The moisture indicator 232 has an inner size of about, but not limited to, 1.18 inches and an outer size of about, but not limited to, 1.45 inches. In one embodiment, the first adhesive film 214 has an inner size of about, but not limited to, 1.18 inches and an outer size of about, but not limited to, 1.9973 inches. In one embodiment, the second adhesive film 212 has an inner size of about, but not limited to, 2.1 inches and an outer size of about, but not limited to, 3 inches. In one embodiment, the third adhesive film 210 has a size of about, but not limited to, 3×3 inches but may be 4 inches by 4 inches. Importantly, the shield is sized for children as well.

Figure 5:
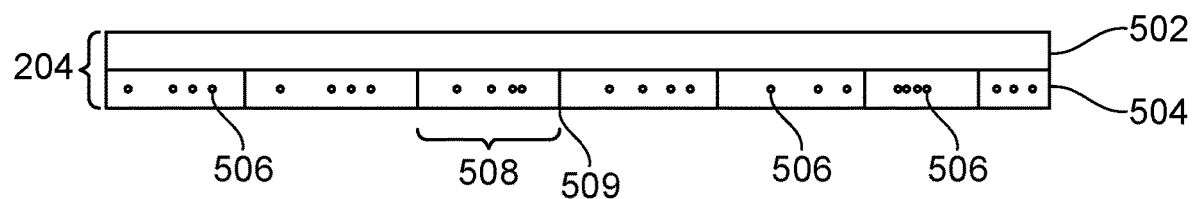
FIG. 5 illustrates a side view of two layers impregnated with microcapsules in accordance with embodiments the present invention.

Now with reference to FIG. 5, a side view of the retention structure 204 is shown. As can be seen, the retention structure 204, toward an inner portion when viewed from the top, may comprise two layers 502 and 504, and have microcapsules (or any carrier) 506 disposed within each conduit 508. The conduits provided internals barriers 509 to keep the capsules and the inner supply or the capuls in place (e.g, anti-bacterial) to prevent downward seepage due to gravity. In this way, the retention structure 204 is prefilled with materials during production. The microcapsules may be filled with anti-infective agents that are safe to the skin but kill bacteria upon touch or proximity.

In operation, the user can activate the microcapsules when pushing down on and applying pressure to the retention structure 204 when applying it to the skin. Thus if, bacteria or fungus gets past the adhesive, the anti-infective kill bacteria or fungus or virus upon touch or proximity.

Figure 6:
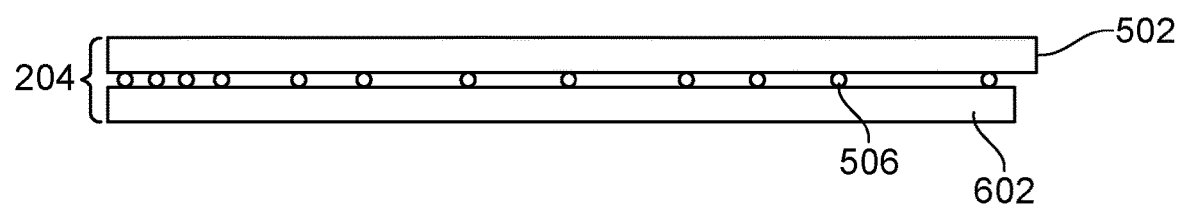
FIG. 6 illustrates a side view of microcapsules disposed in a layer in accordance with embodiments of the present invention.

Referring now to FIG. 6, in this embodiment, the microcapsules 506 are between two layers in the retention structure 204, a first payer 502 and a second layer 602. In operation, the user can activate the microcapsules when pushing down on and applying pressure to the retention structure 204 when applying it to the skin. Thus if, bacteria or fungus gets past the adhesive, the anti-infective agents kill bacteria or fungus or virus upon touch or proximity.

Figure 7:
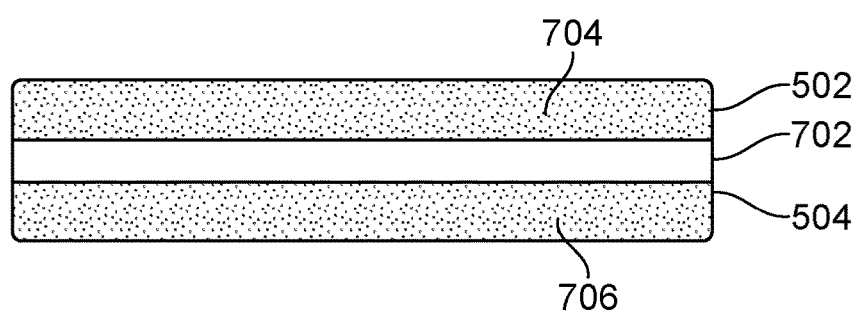
FIG. 7 illustrates a side view of layers impregnated with a gel in accordance with embodiments of the present invention.
Figure 8:
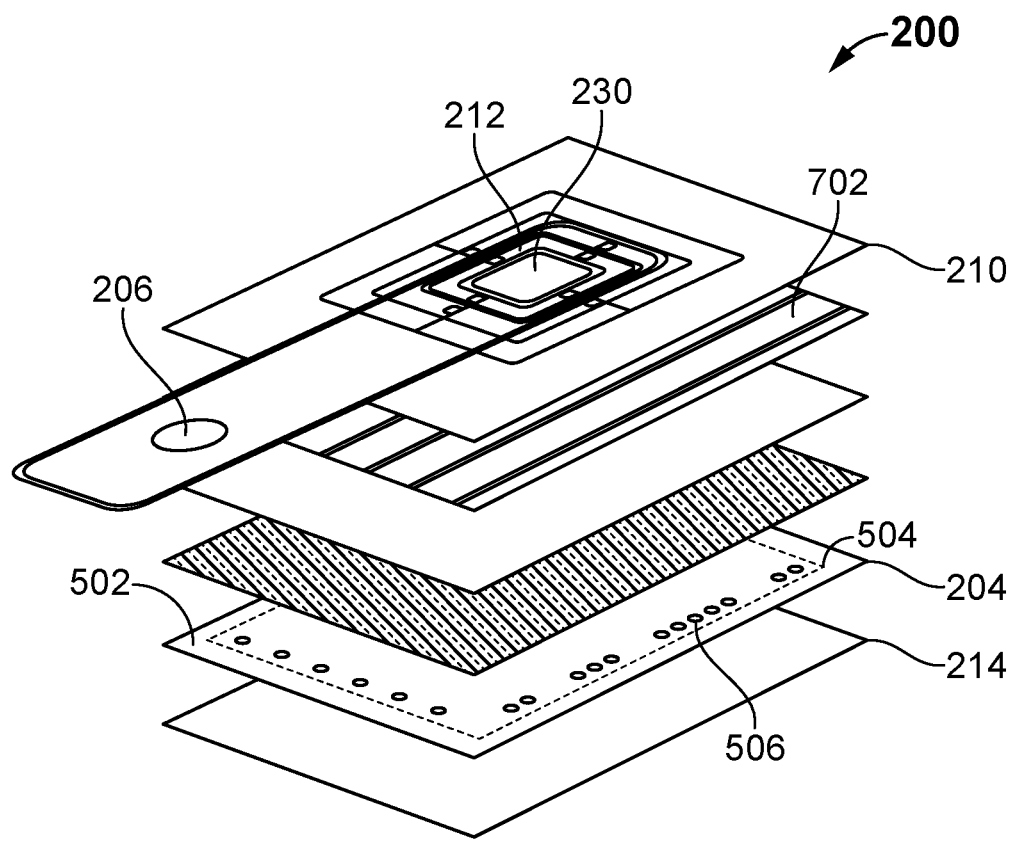
FIG. 8 illustrates an exploded perspective view of the layers of the catheter shield in accordance with an embodiment of the present invention.

Referring now to FIG. 7, in this embodiments, anti-infective agents 704 and 706 may reside in the layer 702 between layer 502 and 504, and the retention structure may be porous so that pressure application allows the gel to seep to the skin of the patient.

Presenting the antigen in the form of microcapsules makes it possible to conserve the antigen under optimum conditions prior to use, to use a wide range of antigens almost independently of any chemical compatibility with the retention structure for given that the antigen isolated within the walls of the microcapsules prior to being opened.

In this way the antigen contained in the microcapsules are selected from substances that are liposoluble and substances that are hydrosoluble. In optional embodiments, the microcapsules have a thin outer wall made of a material selected from porous aminoplast polymers, polyamide polymers, polyurethane polymers, and cellulose polymers; the microcapsules adhere to the filter material by chemical compatibility; the microcapsules adhere to the filter material by means of a chemical binder; and the binder is selected from polyurethane binders, polyamide binders, silicone binders, acrylic binders, and epoxy binders.

Referring now to FIG. 8, an exploded view of the catheter shield showing some, but not all layers, is illustrated. An adhesive layer 214 is provided on retention structure 204. Another microcapsule layer 506 or gel infused layer is provided and covered by layer 502 as described with relation to FIGS. 6-8. Additional adhesive layers (e.g., 212) are provided, and are located on the back side of the sleeve as a thin strip surrounding the sleeve. It is noted that the second adhesive only be located on portions within the diameter of the retention structure 204, or may be located around the entire sleeve 202 in some embodiments.

The catheter shield 200 is designed with patient safety in mind. These affordable, disposable and easy-to-use water barriers cover and protect open wounds, sterile dressings, PICC Lines, stomas, shunts, catheters, colostomies, and more. The catheter shield 200 is economical, reliable and easy to use by patients and/or caregivers, while the patient takes a shower, whilst the impregnated anti-infective layer prevents the catheter shield 200 allows a more simplified positioning of the unit and application of the adhesive mechanism. The catheter shield 200 can vary in shape, size, and length depending on catheter dimensions. The catheter shield 200 reduce the risk of infection from waterborne bacteria by keeping catheter sites and wound dressings dry while showering. The shape and the adhesive layer of the catheter shield 200 allows limited movement of catheter so that the catheter could be worn for a longer time without any inconvenient to users and obviating the bacteria or fungus that may be dangerous to the patient.

While the present invention has been described in connection with what are presently considered to be the most practical and preferred embodiments, it is to be understood that the present invention is not limited to these herein disclosed embodiments. Rather, the present invention is intended to cover all of the various modifications and equivalent arrangements included within the spirit and scope of the appended claims.

Although specific features of various embodiments of the invention may be shown in some drawings and not in others, this is for convenience only. In accordance with the principles of the invention, the feature(s) of one drawing may be combined with any or all of the features in any of the other drawings. The words "including", "comprising", "having", and "with" as used herein are to be interpreted broadly and comprehensively and are not limited to any physical interconnection. Moreover, any embodiments disclosed herein are not to be interpreted as the only possible embodiments. Rather, modifications and other embodiments are intended to be included within the scope of the appended claims.

I claim:

1. A catheter shield comprising:

a sleeve configured to receive and house a proximal end of a catheter projecting from a patient;

a retention structure configured as an outer protective barrier of the catheter shield, wherein the retention structure comprises a first adhesive layer disposed on a bottom portion of the retention structure, wherein the first adhesive layer is configured to detachably bond to the patient's skin;

wherein the sleeve comprises:

a second adhesive layer provided on and surrounding an outer edge of the sleeve, wherein the second adhesive layer is located within a diameter of the retention structure, wherein the second adhesive layer is configured as a middle protective barrier; and a third adhesive layer located within a diameter of the second adhesive, wherein the third adhesive is layer is configured as an inner protective barrier; wherein the third adhesive layer comprises a moisture indicator positioned thereon;

wherein the third adhesive layer comprises a biological indicator configured to allow the patient to see if bacteria is near an insertion point of the catheter;

wherein the retention structure surrounding an outer edge of the sleeve comprises a plurality of conduits having internal barriers therein, wherein the conduits comprise a plurality of microcapsules disposed within each conduit, wherein the microcapsules comprise an anti-infective agent, wherein a user can apply a pressure to the retention structure to release the anti-infective agent if bacteria is near the insertion point.

2. The catheter shield of claim 1, wherein the anti-infective is disposed within the first adhesive layer.

3. The catheter shield of claim 1, further comprising:

a first layer of release paper located on a back of the retention structure;

a second layer of release paper located on a back of the second adhesive;

a third layer of release paper located on a back of the third adhesive;

wherein each of the first, second, and third layers of release paper are releasable by at least one tab disposed on each of the first, second and third layers of release paper.

4. The catheter shield of claim 1, wherein the indicator is formed from a hydrocolloid adhesive, a polyester film, an ethylene oxide, or any combination thereof.

5. The catheter shield of claim 1, wherein the sleeve is made of a fluid-impermeable material that is flexible and configured to cover or house catheter elements connected to the patient's body.

6. The catheter shield of claim 1, wherein the first, second and third adhesives comprise a pressure sensitive acrylic (PSA).

7. The catheter shield of claim 1, wherein the anti-infective comprises hypochlorous acid.

8. The catheter shield of claim 1, wherein the shield is EtO or gamma sterilized.

9. The catheter shield of claim 1, wherein the retention structure is rectangular in shape.

10. The shield of claim 1, wherein the catheter retention structure is a rib for impeding a motion of the proximal end of a catheter.

11. The catheter shield of claim 1, wherein the retention structure comprises two layers, and wherein the anti-infective is disposed between the two layers.

* * * * *